United States Patent [19]
Wickiser

[11] Patent Number: 5,614,525
[45] Date of Patent: Mar. 25, 1997

[54] SALTS OF DISULFONYL METHANE COMPOUNDS WHICH ARE USEFUL AS PARASITICIDE AGENTS

[75] Inventor: David I. Wickiser, Indianapolis, Ind.

[73] Assignee: Eli Lilly and Company, Indianapolis, Ind.

[21] Appl. No.: 434,870

[22] Filed: May 4, 1995

Related U.S. Application Data

[60] Division of Ser. No. 156,123, Nov. 22, 1993, Pat. No. 5,449,681, which is a continuation-in-part of Ser. No. 998,426, Dec. 30, 1992, abandoned.

[51] Int. Cl.$^6$ ................................................ A61K 31/495
[52] U.S. Cl. ...................... 514/255; 514/256; 514/274; 514/326; 514/393; 514/709; 568/30; 568/35
[58] Field of Search ...................... 568/30, 35; 514/709, 514/255, 274, 256, 326, 393

[56] References Cited

U.S. PATENT DOCUMENTS 5,449,681  9/1995  Wickiser.

FOREIGN PATENT DOCUMENTS

| 61061 | 7/1986 | Australia. |
|---|---|---|
| 0209462 | 7/1986 | European Pat. Off.. |
| 2047687 | 3/1980 | United Kingdom. |
| 2049661 | 12/1980 | United Kingdom. |
| 21150 | 4/1993 | WIPO. |

OTHER PUBLICATIONS

R.J. Koshar and R. A. Mitsch, "Bis(perfluoroalkylsulfonyl)-methanes and Related Disulfones," *J. Org. Chem.*, 38(19), 3358–63 (1973).

B. M. Trost and R.A. Kunz, "New Synthetic Reactions. A Convenient Approach to Methyl 3–Oxo–4–pentenoate," *J. Org. Chem.* 39(17), 2648–49 (1974).

A. F. Cunningham and E. P. Kundig, "An Efficient Synthesis of Both Enantiomers of *trans*–1,2–Cyclopentanediol and Their Conversion to Two Novel Bidentate Phosphite and Fluorophosphinite Ligands," *J. Org. Chem.*, 53(8), 1823–25 (1988).

S. S. Magar and P. L. Fuchs, "Bis–Alkylation of Dimetallated Phenylsulfonylmethyl Triflone. A n+1 Annulation Strategy for Synthesis of Cyclic Vinyl Sulfones," *Tetrahedron Lett.*, 33(6), 745–8 (1992).

O. I. Kolodyazhnyi, "Reactions of Phosphines with CH Acids," *Zh. Obshch. Khim.*, 47(4) 956–7 (1977).

N. V. Kondratenko, V. P. Sambur and L. M. Yagupol'skii, "Dual Reactivity of the Silver Salts of Sulfinic Acids," *Zh. Org. Khim.*, 7(11), 2382–8 (1971).

L.M. Yagupol'skii and N.V. Kondratenko, "Arylsulfonyltrifluoromethylsulfonylmethanes," translated from Zhurnal Obshchei Khimii, vol. 33, No. 3, pp. 920–928, Mar., 1963.

Dubenko, et al., "Effectiveness of Derivatives of Mono–, Di–, and Trisulfones in Controlling Plant Diseases," *Fiziol. Akt. Veschechesva*, 10, 102–4 (1978) and translation of same.

Kolodyazhnyi, O.I., "Halophosphonium–Alkylides," *Zhurnal Obschchei Khimii*, vol. 52, No. 5, pp. 1086–1092, May, 1982 and translation of same.

L.M. Yagupol'Skii, et al., "Arylsulfonyl Trifluoromethylsulfonyl methanes," *Chemical Abstracts*, 59, No. 10, 11 Nov. 1963, Columbus, Ohio, U.S.; abstract No. 11689f.

T.A. Sinenko et al., "Antifungal activity of some trisulfones, bis[alkyl](ary)sulfonyl acetonitriles, and their derivatives in vivo," *Chemical Abstracts*, vol. 90, No. 7, 12 Feb. 1979, Columbus, Ohio, U.S.; abstract No. 49439x.

*Primary Examiner*—Johann Richter
*Assistant Examiner*—John Peabody
*Attorney, Agent, or Firm*—Paul R. Cantrell

[57] ABSTRACT

The present invention is directed to the use of disulfonyl methane compounds for the control off parasites in vertebrate animals.

4 Claims, No Drawings

SALTS OF DISULFONYL METHANE COMPOUNDS WHICH ARE USEFUL AS PARASITICIDE AGENTS

CROSS REFERENCE TO RELATED APPLICATION

This application is a division, of application Ser. No. 08/156,123 filed Nov. 22, 1993, now U.S. Pat. No. 5,449,681 which is continuation-in-part of application Ser. No. 07/998,426 filed Dec. 30, 1992, now abandoned.

FIELD OF THE INVENTION

The present invention relates generally to parasiticides, and more particularly to novel methods and compositions for controlling ecto- and endoparasites in vertebrates.

BACKGROUND OF THE INVENTION

The control of ectoparasites, such as fleas, ticks, biting flies and the like, has long been recognized as an important aspect of human and animal health regimes. Traditional treatments were topically applied, such as the famous dips for cattle, and indeed such treatments are still in wide use. The more modern thrust of research however has been towards compounds which can be administered orally or parenterally to the animals and which will control ectoparasitic populations by poisoning individual parasites when they ingest the blood of a treated animal.

The control of endoparasites, or intestinal parasites, has also been an important aspect of human and animal health regimes.

Although a number of ectoparasiticides and endoparasiticides are in use, these suffer from a variety of problems including a limited spectrum of activity, the need for repeated treatment and, in many instances, resistance by parasites. The development of novel endo- and ectoparasiticides is therefore essential to ensure safe and effective treatment of a wide range of parasites over a long period of time.

In addition, there are advantages to controlling both ecto- and endoparasites with one therapeutic agent. For example, a single parasiticidal agent is easier to administer and to incorporate into management regimes. Dosing may also be more accurately controlled. Interfering effects may be eliminated, and in certain circumstances synergistic combinations may be identified and exploited.

A need therefore exists for novel methods of controlling parasites by providing compositions effective for such control when administered orally, parenterally, or topically to a person or animal. The present invention addresses that need.

SUMMARY OF THE INVENTION

In one aspect of the present invention there is provided a method for protecting a vertebrate animal against parasites, which method comprises administering to the animal an effective amount of an active agent which is a compound of Formula I below:

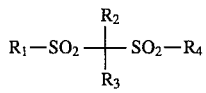
I wherein $R_1$ is a moiety of the formula:

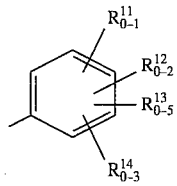

wherein $R^{11}$ is cyano;

$R^{12}$ is nitro, isocyano, $C_2$ to $C_4$ alkanoyl, $C_2$ to $C_4$ perfluoroalkanoyl, 2,2,3,3-tetrafluoropropionyl, —N(hydrogen or $C_1$ to $C_3$ alkyl)$SO_2CF_3$, or —N=C(alkyl of $C_1$ $C_2$, perfluoroalky of $C_1$ to $C_2$, or 1,1,2,2-tetrafluoroethyl, each independently selected)$_2$;

$R^{13}$ is bromo, chloro, or fluoro;

$R^{14}$ is iodo or a group of the formula

—$R^{15}{}_n$—$R^{16}$ wherein n represents 0 or 1, and wherein $R^{15}$ represents

—O—

—S—

—SO—

—$OSO_2$,

—$SO_2$—, or, only when $R^{16}$ represents —$CH_3$,

—$SO_2O$—, and $R^{16}$ represents

—$CF_3$,

—$CF_2CF_2H$,

—$CH_2CF_3$,

—$C_2F_5$, or, only when n is 1 and $R^{15}$ is —SO—, —$SO_2$—, —$OSO_2$—, or —$SO_2O$—, —$CH_3$;

$R_2$ is hydrogen, halogen, $C_1$ to $C_3$ alky, benzyl, or $C_2$ to $C_3$ alkenyl;

$R_3$ is hydrogen or halogen; and $R_4$ is a $C_1$–$C_4$ perfluoroalkyl or 1,1,2,2-tetrafluoroalkyl; such that when $R_1$ contains one or more $R^{11}$, $R^{12}$ or $R^{14}$ substituents, the total number of substituents on $R_1$ is not more than 3.

Alternatively, the method comprises administering a physiologically acceptable salt of a compound of Formula I.

In another aspect of the invention a method of controlling parasites by administering a composition comprising the combination of a compound of Formula I and an additional, known parasiticide is provided.

In addition to the foregoing novel methods, the present invention is directed to certain novel compounds, defined by Formula II below:

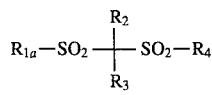
II wherein:

$R_2$, $R_3$ and $R_4$ are as previously defined; and $R_{1a}$ is a moiety of the formula:

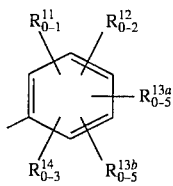

wherein $R^{11}$, $R^{12}$ and $R^{14}$ are as previously defined, $R^{13a}$ is chloro, and $R^{13b}$ is bromo or fluoro;

with the following limitations:

(1) $R_{1a}$ a contains at least one substituent, (2) When $R_{1a}$ contains one or more $R^{11}$, $R^{12}$ or $R^{14}$ substituents, the total number of substituents on $R_{1a}$ is not more than 3, (3) If $R_{1a}$ a contains only one $R^{12}$ substituent, $R_{1a}$ is either polysubstituted or is substituted at either the ortho- or meta-position, and (4) If $R_{1a}$ contains only one $R^{13a}$ substituent, $R_{1a}$ is either polysubstituted or is substituted at either the ortho- or meta-position.

"Poly" in the foregoing definition means three or more. Additionally, the present invention includes the physiologically acceptable salts of the compounds of Formula II.

One object of the present invention is to provide novel methods for controlling parasites in or on vertebrates.

Another object of the present invention is to provide novel compounds useful in such methods.

Further objects and advantages of the present invention will be apparent from the following description of the preferred embodiments.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated herein being contemplated as would normally occur to one skilled in the art to which the invention pertains.

The present invention is directed to the prevention and treatment of parasitic attack on host animals and provides a new tool for the control of parasitic organisms. In particular, the present invention provides a method of controlling parasites by administering a member of the class of compounds known generally as disulfonyl methanes. Most particularly, the present invention relates to methods of controlling parasites in vertebrates by administering one or more compounds represented generally by Formula I below:

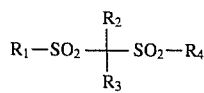

wherein $R_1$, $R_2$, $R_3$ and $R_4$ are as previously defined.

The treatment is particularly effective against hematophagous organisms which attack their hosts by ingesting blood. By "ingesting" is meant not only those parasites which pierce and suck the blood from a circulatory system, but also those parasites, typically arthropods, which consume tissue or tissue fluids of the host and thereby inevitably consume blood or blood constituents.

The present compounds may also be useful in a yet other method in which the same active agent as above defined is employed as a "feed through larvicide." In this method, the compound is administered to a vertebrate animal, especially a warm blooded animal, in order to inhibit parasitic organisms which live in the feces of the animal. Such organisms are typically insect species in the egg or larval stage.

Accordingly, it can be seen that the present methods can be utilized for protection against a wide range of parasitic organisms. Further, it should be noted that protection is achieved in animals with existing parasitic infections by eliminating the existing parasites, and/or in animals susceptible to attack by parasitic organisms by preventing parasitic attack. Thus, protection includes both treatment to eliminate existing infections and prevention against future infestations.

Representative parasitic organisms include the following:

Platyhelminthes:
  Trematoda such as:
    Clonorchis
    Echinostoma
    *Fasciola hepatica* (liver fluke)
    *Fascioloides magna*
    Fasciolopsis
    Metgonimus
    Paragonimus
    Schistosoma spp.

Nemathelminthes:
  Ancylostomum
  Angiostrongylus
  Anisakis
  Ascaris
  Brugia
  Bunostomum
  Cooperia
  Dictyocaulus (lungworm)
  Dipetalonema
  Dirofilaria (heartworm)
  Dracunculus
  Elaeophora
  Gaigeria
  *Globocephalus urosubulatus*
  Haemonchus
  Metastrongylus (lungworm)
  Muellerius (lungworm)
  *Necator americanus*
  Onchocerca
  Ostertagia
  Protostrongylus (lungworm)
  Setaria
  Stephanofilaria
  Syngamus
  Toxascaris
  Toxocara
  Trichinella
  *Uncinaria stenocephala*
  *Wucheria bancrofti*

Arthropoda
  Crustacea
    Argulus
    Caligus
  Arachnida
    *Amblyomma americanum* (Lone-star tick)

*Amblyomma maculatum* (Gulf Coast tick)
*Argas persicus* (fowl tick)
*Boophilus microplus* (cattle tick)
*Demodex bovis* (cattle follicle mite)
*Demodex canis* (dog follicle mite)
*Dermacentor andersoni* (Rocky Mountain spotted fever tick)
*Dermacentor variabilis* (American dog tick)
*Dermanyssus gallinae* (chicken mite)
*Ixodes ricinus* (common sheep tick)
*Knemidokoptes gallinae* (deplumming mite)
*Knemidokoptes mutans* (scaly-leg mite)
*Otobius megnini* (ear tick)
*Psoroptes equi* ( scab mite )
*Psoroptes ovis* (scab mite)
*Rhipicephalus sanguineus* (brown dog tick)
*Sarcoptes scabiei* (mange mite)

Insecta
Aedes (mosquito)
Anopheles (mosquito)
Culex (mosquito)
Culiseta (mosquito)
*Bovicola bovis* (cattle biting louse)
*Callitroga hominivorax* (blowfly)
Chrysops spp. (deer fly)
*Cimex lectularius* (bed bug)
*Ctenocephalis canis* (dog flea)
*Ctenocephalis felis* (cat flea)
Culicoides spp. (midges, sandflies, punkies, or no-see-ums)
*Damalinia ovis* (sheep biting louse)
Dermatobia spp. (warble fly)
Dermatophilus spp. (fleas)
*Gasterophilus haemorrhoidalis* (nose bot fly)
*Gasterophilus intestinalis* (common horse bet fly)
*Gasterophilus nasalis* (chin fly)
Glossina spp. (tsetse fly)
*Haematobia irritans* (horn fly, buffalo fly)
*Haematopinus asini* (horse sucking louse)
*Haematopinus eurysternus* (short nosed cattle louse)
*Haematopinus ovillus* (body louse)
*Haematopinus suis* (hog louse)
*Hydrotaea irritans* (head fly)
*Hypoderma bovis* (bomb fly)
*Hypoderma lineatum* (heel fly)
*Linognathus ovillus* (body louse)
*Linognathus pedalis* (foot louse)
*Linognathus vituli* (long nosed cattle louse)
Lucilia spp. (maggot fly)
*Melophagus ovinus* (sheep ked)
*Oestrus ovis* (nose bot fly)
*Phormia regina* (blowfly)
Psorophora
Reduvirus spp. (assassin bug)
Simulium spp. (black fly)
*Solenopotes capillatus* (little blue cattle louse)
*Stomoxys calcitrans* (stable fly)
Tabanus spp. (horse fly)

Parasitic organisms which live in feces are typically he egg and larval stages of insects such as

*Musca domestica* (housefly)

*Musca autumnalis* (face fly)

Haematobia spp. (horn fly, buffalo fly and others).

In the control of parasites, combinations of parasiticidal agents are frequently used to minimize the development of resistance, to increase the spectrum of parasite control, and to minimize the risk of side effects. Therefore, the present invention is also directed to methods of controlling parasites in vertebrates by administering a composition which is the combination of a compound of Formula I, or one of the physiologically acceptable salts thereof, and one or more known parasiticides. As can be seen by those skilled in the art, known parasiticides appropriate for use in the present invention include both anthelmintics (endectocides) and ectoparasiticides. Preferred combinations are those with anthelmintics.

Representative known parasiticides with which the present compounds can be combined include the following:

among the anthelmintics:
albendazole
bephenium
bunamidine
coumaphos
dichlorvos
diethylcarbamazine
epsiprantel
febantel
fenbendazole
flubendazole
ivermectin
levamisole
mebendazole
milbemycin
morantel
moxidectin
netobimin
niclosamide
nicotine
nitroscanate
oxfendazole
oxibendazole
piperazine
praziquantel
pyrantel
ricobendazole
tetramisole
thiabendazole among the flukicides:
clorsulon
closantel
diamphenethide
nitroxynil
oxyclozanide
rafoxanide
triclabendazole among the ectoparasiticides:
alphamethrin
amitraz
coumaphos
cycloprothrin
cyfluthrin
cyhalothrin
cypermethrin
cyromazine
deltamethrin
diazinon
diflubenzuron
dioxathion
fenthion
fenvalerate
flucythrinate
flumethrin
ivermectin
methoprene metriphonate
moxidectin
permethrin
phosmet
pirimiphos
propetamphos
propoxur
rotenone
temephos
tetrachlorvinphos Preferred known parasiticides for such combinations are the anthelmintics, and especially the following:

albendazole, fenbendazole, flubendazole, levamisole, mebendazole, morantel, oxfendazole, oxibendazole, piperazine, pyrantel, ricobendazole, thiabendazole, and triclabendazole.

The amount of present active agent which is to be employed is not critical and will vary with the identity of the host, the identity of the parasite, the route of administration, whether single or multiple dosing is employed, and other factors known to those skilled in the art. For single dosing, a dose of from 1.0 mg/kg to 50 mg/kg, and preferably from 5 mg/kg to 40 mg/kg, will generally be effective. In situations where the host is subject to continuing parasitic pressure, it is generally preferred that the compound of the present invention be administered more than once, such as intermittently over the period of time that the host is subject to parasitic attack. This may be for a brief period of days or several weeks, for a season, or up to a lifetime. Sustained release formulations providing delivery over a period of time are therefore often preferred. When repeated dosing is employed, the compounds can be used at lower rates, such as from 0.1 to 10 mg/kg per day. All doses described above relate to the amount of the parent compound represented by Formula I. When a salt is employed, a correspondingly higher amount should be used to provide the indicated amount of the parent compound. As an exception, when the salt is with a parasiticidally active compound such as levamisole, the amount of the parent compound of Formula I may be reduced.

For the control of blood-ingesting parasites, the present compounds must be delivered in a manner to enter and spread through the circulatory system of the host. However, it has been found that this can be achieved by any of numerous means such as intramuscular, intraruminal, intravenous, oral, subcutaneous, and transdermal administration. If the compound is delivered orally or intraruminally, it may be desirable to protect the compound during its passage through the rumen. Techniques for achieving this are well known to those skilled in the art.

For some modes of delivery, such as in gelatin capsules, the present compounds can be employed neat. However, for most delivery techniques the compounds are formulated with one or more physiologically acceptable carriers. Formulation techniques are well known in medical and veterinary practice, and can readily be chosen for the present invention by those skilled in the art. For oral delivery the compounds can be formulated in solid forms such as chewable or non-chewable tablets, capsules and pastes, or in liquid forms such as syrups, aqueous suspensions, solutions, drenches and the like. The compounds can also be formulated as boluses. With appropriate design and formulation, the bolus will remain in the rumen of ruminants and provide continued payout of the compounds of the present invention over a period of time.

The compounds are conveniently administered to livestock animals via a feedstuff, via the drinking water, or via a mineral block. In the case of feedstuffs, the compound is typically incorporated in a premix which is subsequently added to other feed components to form the finished feed. The compounds can also be formulated as part of the drinking water.

The compounds can also be administered by intraruminal, intramuscular, intravenous, or subcutaneous injection. Typically the compound is formulated in a vehicle of lipophilic nature such as an animal or vegetable oil. Parenteral formulations which provide delayed delivery can also be used in delivering the present compounds.

In all of the foregoing formulations, the compounds are mixed with physiologically acceptable carriers suited for the particular mode of delivery. The concentration of the present compound is not critical and will vary with the particular mode of delivery. Thus, the concentration may range from 0.1 to 95 percent weight/volume; and in many instances from 1 to 50 percent weight/volume.

In the methods of the present invention, certain of the compounds are preferred over others. For example, compounds preferred in testing to date include:

[((3,5-bistrifluoromethyl)phenyl)sulfonyl][(trifluoromethyl)sulfonyl]methane;

[(3,4-dichlorophenyl)sulfonyl][(trifluoromethyl)sulfonyl]dichloromethane;

[(2,4-dichlorophenyl)sulfonyl][(trifluoromethyl)sulfonyl]methane;

[(3,5-dichlorophenyl)sulfonyl][(trifluoromethyl)sulfonyl]methane;

[(4-fluorophenyl)sulfonyl][(trifluoromethyl)sulfonyl]methane;

[(2,6-dichlorophenyl)sulfony][(trifluoromethyl)sulfonyl]methane;

[(phenyl)sulfonyl][(trifluoromethyl)sulfonyl]methane;

[(4-trifluoromethoxyphenyl)sulfonyl][(trifluoromethyl)sulfonyl]methane;

[(4-chlorophenyl)sulfonyl][(trifluoromethyl)sulfonyl]methane;

[(3,4-dichlorophenyl)sulfonyl][(trifluoromenthyl)sulfonyl]methane;

[(2-chlorophenyl)sulfonyl][(trifluoromethyl)sulfonyl]methane;

[((4-trifluoromethyl)phenyl)sulfonyl][(trifluoromethyl)sulfonyl]methane;

[((3-trifluoromethyl)phenyl)sulfonyl][(trifluoromethyl)sulfonyl]methane;

[(4-cyanophenyl)sulfonyl][(trifluoromethyl)sulfony]methane;

[(4-bromophenyl)sulfonyl][(trifluoromethyl)sulfonyl]methane;

[(2,4,5-trichlorophenyl)sulfonyl][(trifluoromethyl)sulfonyl]methane;

[(3-chloro-4-fluoro-phenyl)sulfonyl][(trifluoromethyl)sulfonyl]methane; and

[(pentachlorophenyl)sulfonyl][(trifluoromethyl)sulfonyl]methane.

Especially preferred compounds include:
[((3,5-bistrifluoromethyl)phenyl)sulfonyl][(trifluoromethyl)sulfonyl]methane;
[(4-fluorophenyl)sulfonyl][(trifluoromethyl)sulfonyl]methane;
[(2,4-dichlorophenyl)sulfonyl][(trifluoromethyl)sulfonyl]methane;
[(phenyl)sulfonyl][(trifluoromethyl)sulfonyl]methane;
[(4-chlorophenyl)sulfonyl][(trifluoromethyl)sulfonyl]methane;
[(3,4-dichlorophenyl)sulfonyl][(trifluoromethyl)sulfonyl]methane;
[((4-trifluoromethyl)phenyl)sulfonyl][(trifluoromethyl)sulfonyl]methane;
[((3-trifluoromethyl)phenyl)sulfonyl][(trifluoromethyl)sulfonyl]methane;
[(2,4,5-trichlorophenyl)sulfonyl][(trifluoromethyl)sulfonyl]methane;
[(3-chloro-4-fluorophenyl)sulfonyl][(trifluoromethyl)sulfonyl]methane;
[(pentachlorophenyl)sulfonyl][(trifluoromethyl)sulfonyl])-methane;
[(4-trifluoromethoxyphenyl)sulfonyl][(trifluoromethylsulfonyl]methane; and
[(3,4-dichlorophenyl)sulfonyl][(trifluoromethyl)sulfonyl]dichloromethane.

As noted above, the compounds of the present invention can be employed in the form of physiologically acceptable salts. The identity of the salt moiety is not critical. Suitable salts include the following:

alkali metal;

alkaline earth metal;

ammonium and substituted ammonium such as mono-, di-, tri- or tetra-alkylammonium, such as those containing a total of from 1 to 40 carbon atoms, and preferably not more than 25 carbon atoms; and anthelmintics which are basic, preferably
bephenium,
diethylcarbamazine,
levamisole,
morantel,
nicotine,
piperazine, and
pyrantel.

The salts with anthelmintics are a preferred embodiment, in that the anthelmintic efficacy of the salt moiety complements the predominantly ectoparasiticidal activity of the disulfonyl methanes. Although such complementation can also be achieved by simple mixtures of the disulfonyl methane and the anthelmintic, it is often preferred to employ the salt form. Salts with anthelmintic bases are therefore a preferred embodiment, including for those compounds of Formula I which are not included in Formula II, for example

[phenylsulfonyl][(trifluoromethyl)sulfonyl]methane;
[(4-chlorophenyl)sulfonyl][(trifluoromethyl)sulfonyl]methane;
[(4-nitrophenyl)sulfonyl][(trifluoromethyl)sulfonyl]methane; and
[(3-nitro-4-chlorophenyl)sulfonyl][(triflouromethyl)sulfonyl]methane.

Thus, another embodiment of the present invention is a salt of one or these four compounds with an anthelmintic base selected from the group consisting of
bephenium,
diethylcarbamazine,
levamisole,
morantel,
nicotine,
piperazine, and
pyrantel.

Especially preferred salts are those with levamisole.

In addition, compositions comprising a combination of a compound of Formula I and a known parasiticide such as those identified above are included within the scope of the present invention. Preferred combinations include a compound according to Formula I and a known parasiticide selected from the group consisting of:
albendazole,
fenbendazole,
flubendazole,
levamisole,
mebendazole,
morantel,
oxfendazole,
oxibendazole,
piperazine,
pyrantel,
ricobendazole,
thiabendazole, and
triclabendazole.

previously stated, such compositions allow enhanced control of parasites.

As previously indicated, the compositions of the present invention may be formulated to accomplish therapeutic delivery in vertebrates. Appropriate formulations for a particular composition depend on the parasite to be controlled, the host to be protected, etc., and may be determined by those skilled in the art without undue experimentation.

The compounds of Formula I are in some cases known compounds; all of them are prepared in known synthetic techniques. The most general synthetic pathway, essentially that utilized in *Zh. Org,. Khim.*, 33(3), 920–928 (1963), is as follows:

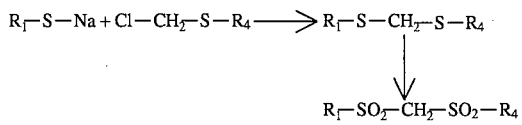

In the initial reaction, a benzenethiol and a substituted methyl chloride are condensed to prepare the intermediate

The reaction is conveniently carried out in a reaction medium such as a loweralkanol, and at temperatures of about 50° to 80° C. The resulting intermediate is then oxidized to convert it to the corresponding compound of Formula I. A preferred oxidizing agent is 30% hydrogen peroxide in trifluoroacetic acid; however, chromium trioxide, $CrO_3$, can also be used as oxidizing agent, in acetic acid. Reaction temperatures of about 25° to 100° C. are generally used.

Other synthetic techniques are available and can be used to make many of the compounds of Formula I. One such technique is as follows:

$R_1SO_2CH_3 + (R_4SO_2)_2O \rightarrow R_1SO_2CH_2SO_2R_4$

This procedure is desirably used for compounds wherein $R_4$ is trifluoromethyl. The reactants and butyl lithium should be mixed in a reaction medium such as ether, at temperatures of about −100° to −50° C. Alternately, the $R_1SO_2CH_3$ starting material is reacted with $K^+{}^-N(SiMe_3)_2$ and phenyl-$N(SO_2CF_3)_2$ in a reaction medium such as tetrahydrofuran and at temperatures of about 60° to 70° C.

Another alternate synthetic technique for many of the compounds is as follows:

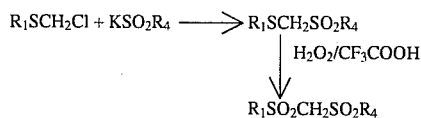

The foregoing three techniques are employed to prepare the compounds of Formula I wherein $R_2=R_3=$hydrogen.

Those compounds where either or both of $R_2$ and $R_3$ are other than hydrogen are prepared by halogenating or alkylating the corresponding $R_2=R_3=$hydrogen compound, as illustrated by Examples 3 and 4, below. Compounds wherein $R_1$ contains an $R^{12}$ substituent that is isocyano, —N(hydrogen or $C_1$ to $C_3$ alkyl)$SO_2CF_3$, or —N=C(alkyl of $C_1$ to $C_2$, perfluoroalkyl of $C_1$ to $C_2$, or 1,1,2,2-tetrafluoroethyl, each independently selected)$_2$, are preferably prepared from the corresponding nitro-substituted compound in standard techniques.

Salts are prepared in standard methods. Thus, a compound of Formula I wherein $R_2=R_3=$hydrogen is reacted with the desired base, or the desired base is reacted with a compound of Formula I as its sodium salt.

When $R^{15}$ represents "—$OSO_2$—", it is the oxygen which is attached to the phenyl ring:

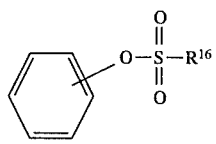

and $R^{16}$ can be any of the listed moieties. When $R^{15}$ represents "—$SO_2$—", it is the sulfur which is attached to the phenyl ring:

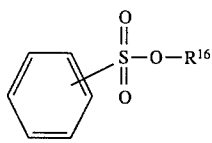

and $R^{16}$ is methyl, only.

The following examples are illustrative of the processes which may be used to prepare the compositions; no limitation to the scope of the invention is intended thereby.

EXAMPLE 1

Preparation of [(3,4-dichlorophenyl)sulfonyl][(trifluoromethyl)sulfony]methane

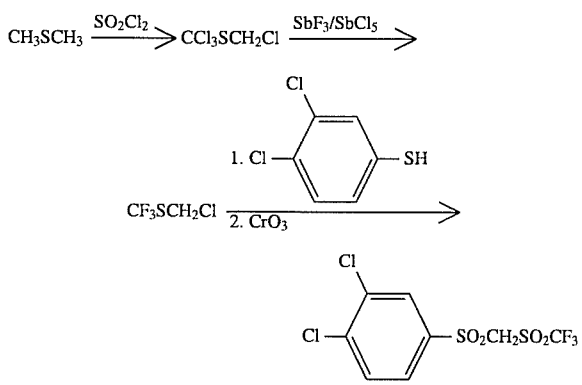

The intermediate product $CCl_3SCH_2Cl$ was prepared according to McBee, 74 *J. Am. Chem. Soc.* 3594 (1952). Twenty grams of dimethyl sulfide was placed in a three-necked flask in an ice bath with additional funnel and scrubber. $SO_2Cl_2$ (192 g) was added at 5° C. (temperature rose to 20° C.), the mixture was warmed to room temperature and was then heated over two hours to 95° C. Heating continued at 90°–100° C. for six hours. The mixture was stirred overnight. The mixture was distilled at atmospheric pressure to obtain $CCl_3SCH_2Cl$. Fraction 1—145°–150° C.; fraction 2—175°–185° C. NMR showed product plus 5% $CCl_3SCH_3$ compound.

Yield=41 g (64%).

$SbF_3$ (35.5 g) and $SbCl_5$ (1 g) were combined in a three-necked flask in a 20° C. water bath. Twenty grams of $CCl_3SCH_2Cl$ was added over 15 minutes. The mixture was heated in a water bath to 80° C. and maintained at 80°–90° C. for 2 hours. $CF_3SCH_2Cl$ distillate was collected at 45°–50° C.

NaOMe (2.9 g, 0.053 moles) was placed in 25 ml methanol, and 9.5 g (0.053 moles) of 3,4-dichlorobenzenethiol was added slowly thereto. Eight grams of starting material ($CF_3SCH_2Cl$) were added dropwise, with refluxing for two hours. The material was stirred overnight at room temperature, poured into $H_2O$ and extracted with ether. The product was washed and dried and used in the following procedure.

$CrO_3$ (23.8 g, 0.24 moles) in 55 ml AcOH was added dropwise to the extracted product (8.7 g, 0.03 moles in 10 ml AcOH) over two hours with the temperature being maintained below 40° C. After heating slowly to 80° C., the mixture was maintained at that temperature for an additional 1.5 hours, poured into 400 ml $H_2O$, and collected. The material was dissolved in $CH_2Cl_2$ washed with water until all green color disappeared. A white solid was produced after drying and evaporation of the $CH_2Cl_2$. Crude yield was 8.7 g. This material was stirred in isopropanol (mp 129°–131° C.), giving a yield of 5.7 g. (Theoretical analysis: C—26.90%; H—1.41%. Actual analysis: C—27.08%; H—1.42%.)

Similar disulfonyl methanes may be synthesized according to the above synthetic pathway by substituting the appropriate starting material for 3,4-dichlorobenzenethiol. Appropriate starting materials for a particular disulfonyl methane may be selected by one of ordinary skill in the art without undue experimentation.

EXAMPLE 2

Preparation of [(4-trifluoromethoxyphenyl)sulfonyl][(trifluoromethyl)sulfonyl]methane

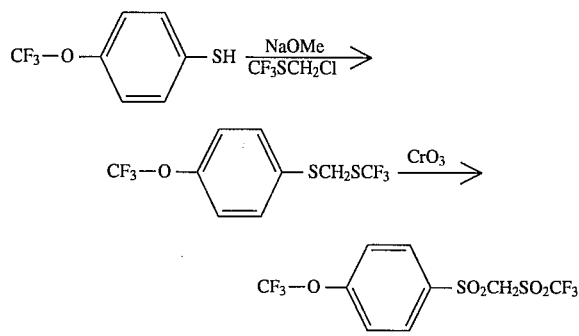

750 mg NaOMe (0.0139 moles) in approx. 12 ml MeOH was slowly added to 2.70 g starting material (0.139 moles). CF$_3$SCH$_2$Cl (2.09 g) was added dropwise. The mixture was refluxed for two hours and stirred overnight at room temperature. The product was then poured into water, extracted twice with ether, washed with water, dried with MgSO$_4$ and evaporated to remove the solvent. Yield: 3.05 g.

13.6 g starting material prepared as in the previous paragraph was dissolved in 15 ml AcOH and added dropwise to 35.3 g CrO$_3$(0.353 moles, 8 eq.) in 150 ml AcOH at room temperature. The mixture was stirred overnight at room temperature, poured into 400 ml ice water, stirred for twenty minutes and filtered. The precipitate was collected and washed several times with H$_2$0. 18.2 g of product (wet) was recrystallized from 120 ml EtOH. The fractions were combined (8.5 g total) in approx. 15 ml MeOH. CrO$_3$ (5.5 g, 2 eq.) was added dropwise and the mixture was refluxed between 70°–80° C. for about two hours. The above work up was repeated. Product was obtained after recrystallization with isopropanol, m.p., 103°–105° C.

EXAMPLE 3

Preparation of 1-[(4-trifluoromethoxyphenyl)sulfonyl]1-[(trifluoromethyl)sulfonyl]ethane

[(4-trifluoromethoxy)phenyl]sulfonyl][(trifluoromethyl) sulfonyl]methane (1.0 g), potassium carbonate (460 mg), and methyl iodide (400 g) were mixed in 20 ml of DMF and the reaction mixture stirred for 4 hours. Another 200 mg of methyl iodide was added and the reaction mixture was stirred over a weekend (all of the foregoing at ambient temperature of about 25° C.). The reaction mixture was then poured into water and filtered. The filtrate was acidified. The desired product precipitated and was collected. It was purified by HPLC (90% hexane, 10% ethyl acetate eluent). It melted at 77°–80° C.

EXAMPLE 4

Preparation of [(3,4-dichlorophenyl)sulfonyl][(trifluoromethyl)sulfonyl]dichloromethane

[(3,4-dichlorophenyl)sulfonyl][(trifluoromethyl)sulfonyl] methane (500 mg) was reacted with excess sulfuryl chloride in acetic acid (20 ml). The reaction mixture was heated for about an hour to 60° C., then poured into a volume of water and the product collected. It was recrystallized twice from ethanol, m.p., 85°–87° C.

EXAMPLE 5

Preparation of [phenylsulfonyl][(trifluoromethyl)sulfonyl]methane

CF$_3$SO$_2$K (1 g) was mixed with 6 ml of acetonitrile and phenyl (chloromethyl) sulfide (780 mg) was added dropwise over a period of time. The reaction mixture was refluxed overnight and worked up to obtain the desired (phenylthio) [(trifluoromethyl)sulfonyl]methane as a dark oil. Identity of the compound was confirmed by NMR and IR.

This compound was mixed with 5 m of trifluoroacetic acid and 5 ml of hydrogen peroxide (30%). The reaction mixture was heated to 75° C. for an hour; the reaction mixture was then cooled, 50 ml of water was added, and the precipitated product was collected. It was recrystallized from hexane, m.p., 71°–73° C.

EXAMPLE 6

Preparation of [(3,4-dichlorophenyl)sulfonyl][(perfluorobutyl)sulfonyl]methane

[(3,4-dichlorophenyl)sulfonyl][perfluorobutyl)sulfonyl] methane was synthesized by reacting 3,4-dichlorophenyl methyl sulfone with butyl lithium and then adding perfluorobutyl sulfonyl fluoride. Two grams of 3,4-dichlorophenyl methyl sulfone was placed in 100 ml ether and 3.6 ml of butyl lithium was added dropwise. The mixture was cooled to −70° C., and 1.3 g of CF$_3$CF$_2$CF$_2$CF$_2$SO$_2$F was added slowly. The mixture was stirred for 1 hour, water was added, and the ether was evaporated away. A white solid was extracted with 10% Na$_2$CO$_3$. The product was acidified and collected, m.p., 105°–107° C. NMR indicated [(3,4-dichlorophenyl)sulfonyl][(perfluorobutyl)sulfonyl]methane product.

EXAMPLE 7

Preparation of Sodium Salt of [(3,4-dichlorophenyl)-sulfonyl][(trifluoromethyl)sulfonyl]methane The sodium salt of [(3,4-dichlorophenyl)sulfonyl][(trifluoromethyl)sulfonyl]methane was prepared as follows. 2.9 g (0.0081 mole) of [(3,4-dichlorophenyl)sulfonyl][(trifluoromethyl)sulfonyl]methane and sodium methoxide (0.44 g; 0.0081 mole) were reacted in 100 ml of methanol. The reaction mixture was stirred overnight at room temperature, then filtered and the methanol evaporated to obtain the desired product, m.p. 178° C.–182° C.

EXAMPLE 8

Preparation of Levamisole Salt of [(3,4-dichlorophenyl)sulfonyl][trifluoromethyl) sulfonyl]methane Two grams (0.0053 mole) of [(3,4-dichlorophenyl)sulfonyl][(trifluoromethyl)sulfonyl]methane and 300 mg (0.005 mole) sodium methoxide were reacted in 100 ml of methanol. The reaction mixture was stirred for ten minutes at room temperature, and the methanol was evaporated. Ten to fifteen ml of water were added and the solution was filtered into a solution of 1.4 g (0.0058 mole) levamisole HCl in 50 ml H$_2$O. The precipitate which immediately forms was collected and washed in isopropanol to obtain the desired product. The solid was analyzed by NMR and elemental analysis, which confirmed the formation of the levamisole salt, m.p., 109°–112° C.

Representative compounds to be employed in the present invention, and which may be prepared by the foregoing procedures, include the following:

TABLE 1

$$\text{Phenyl-SO}_2-\underset{R_3}{\overset{R_2}{C}}-SO_2-R_4$$

| Substitution on Phenyl Ring | $R^2$ | $R^3$ | $R^4$ | m.p. °C. |
|---|---|---|---|---|
| 3,5-dichloro | H | H | $CF_3$ | 108–110 |
| pentachloro | H | H | $CF_3$ | 164–166 |
| 4-fluoro | H | H | $CF_3$ | 82–84 |
| 2,4-dichloro | H | H | $CF_3$ | 93–95 |
| 3,5-bis(trifluoromethyl) | H | H | $CF_3$ | 110–111 |
| 4-trifluoromethyl | H | H | $CF_3$ | 119–122 |
| 2,4,5-trichloro | H | H | $CF_3$ | 122–125 |
| 3-chloro-4-fluoro | H | H | $CF_3$ | 109–111 |
| 3-trifluoromethyl | H | H | $CF_3$ | 98–100 |
| 2,6-dichloro | H | H | $CF_3$ | 77–79 |
| 2-chloro | H | H | $CF_3$ | 101–104 |
| 4-cyano | H | H | $CF_3$ | 134–136 |
| 4-bromo | H | H | $CF_3$ | 130–131 |
| 4-chloro | H | H | $CF_3$ | lit., 121 |
| 4-chloro | H | Na | $CF_3$ | 240–244 |
| 2,4-dichloro | H | Na | $CF_3$ | 250–253 |
| 3,5-bis(trifluoromethyl) | H | Na | $CF_3$ | 230 (d.) |
| 4-bromo | H | Na | $CF_3$ | 246–247 |
| 4-nitro | H | H | $CF_3$ | lit., 150–151 |
| 4-(trifluoromethoxy) | H | levamisole | $CF_3$ | 78–79 |
| 3,4-dichloro | H | $CH_3$ | $CF_3$ | 102–104 |
| 2-nitro-4-(trifluoromethyl) | H | H | $CF_3$ | 125–127 |
| 3,4-dichloro | H | tetramethylammonium | $CF_3$ | 103–107 |
| 4-(trifluoromethoxy) | H | tetramethylammonium | $CF_3$ | 115–117 |
| 4-(trifluoromethoxy) | H | Na | $CF_3$ | 236–239 |
| 4-$OSO_2CF_3$ | H | H | $CF_3$ | 95–97 |
| 4-(trifluoromethoxy) | H | tetra-n-butylammonium | $CF_3$ | oil |
| 3,4-dichloro | H | H | $CF_3$ | oil |
| 4-bromo | H | K | $CF_3$ | 279–281 (dec) |

Reference will now be made to specific examples of the methods of the present invention. It is to be understood that the examples are provided to more completely describe preferred embodiments, and that no limitation to the scope of the invention is intended thereby.

EXAMPLE 9

Tests Against *Phormia Regina* (blow fly) and *Stomoxys Calcitrans* (stable fly)

Various of the compounds to be employed in the present invention were evaluated in preliminary tests for the control of the adult stage of *Stomoxys calcitrans* (stable fly). This preliminary test employed a stock solution of the respective compound. This same test was also conducted as an adjunct to in vivo tests reported below. In this instance, the test employed serum (or in some cases, whole blood) from treated animals or from serum spiked with a compound. The preliminary test was conducted against only adult *Stomoxys calcitrans* (stable fly); testing of serum or whole blood was against both *Stomoxys calcitrans* as well as *Phormia regina* (blow fly). The test procedures were as follows.

The compound to be evaluated was dissolved in 1 part acetone/1 part ethanol to provide a stock solution of the compound at a concentration of 5,000 ppm; if necessary, this solution was placed in a sonicator for 15 minutes. Portions of the stock solution were placed in 15 ml test tubes, and portions of bovine serum were added to provide the desired dilution of the test compound. Alternately, a sample of serum or blood was used and placed in the test tubes. A dental wick was placed in each test tube and the serum allowed to saturate the wick.

For the blow fly test, approximately 20 blow fly larvae were placed on the top center of the saturated dental wick and the test tube was plugged with cotton and incubated am 80° F. and 80% humidity for 48 hours. Larval mortality counts were made at each of 24 and 48 hours to determine percent efficacy against blow flies.

For the adult stable fly test, the saturated wick was placed in a 1.5 inch$^2$ weigh dish on a filter paper in a petri dish and approximately 10 chilled live, hungry stable flies were placed on the center of the dish bottom. The dish was covered and allowed to incubate at 80° F. and 80% relative humidity for 48 hours. Mortality readings were made at each of 24 and 48 hours to determine percent efficacy against adult stable fly.

The results of blow fly and stable fly tests indicate that compounds according to Formula I are effective against blood sucking parasites such as insects. Further, the following compounds were shown to be particularly effective in this regard:

[((3,5-bistrifluoromethyl)phenyl)sulfonyl][(trifluoromethyl) sulfonyl]methane;

(4-fluorophenyl)sulfonyl][(trifluoromethyl)sulfonyl] methane;

[(2,4-dichlorophenyl)sulfonyl][(trifluoromethyl)sulfonyl] methane;

[(phenyl)sulfonyl][(trifluoromethyl)sulfonyl]methane;

[(4-trifluoromethoxyphenyl)sulfonyl][(trifluoromethyl)-sulfonyl]methane;

[(3,4-dichlorophenyl)sulfonyl][(trifluoromethyl)sulfonyl] methane;

[((4-trifluoromethyl)phenyl)sulfonyl][(trifluoromethyl)-sulfonyl]methane;

[(2,4,5-trichlorophenyl)sulfonyl][(trifluoromethyl)sulfonyl]methane;

[(3-chloro-4-fluoro-phenyl)sulfonyl][(trifluoromethyl)-sulfonyl]methane;

[(4-chlorophenyl)sulfonyl][(trifluoromethyl)sulfonyl] methane

[((3-trifluoromethyl)phenyl)sulfonyl][(trifluoromethyl)-sulfonyl]methane;

[(pentachlorophenyl)sulfonyl][(trifluoromethyl)sulfonyl] methane.

EXAMPLES 10–24

Tests Against Worms Such as *Haemonchus Contortus* in Sheep and Cattle

Representative compounds to be employed in the present invention were evaluated in parasitized sheep and cattle. The animals were naturally infected with *Haemonchus contortus* and often times were additionally infected with other species. The evaluations were carried out as follows. The respective compound was formulated, generally by simply dissolving it in polyethylene glycol 200 (PEG 200 Formulation). The formulations were administered to the test animal as a single injection, either intraruminal or subcutaneous, or as a continuous intraruminal infusion. Typically there were two animals in each treatment group and one-two animals in the vehicle control group. Fecal material was collected daily both pre- and post-treatment, and the number of nematode eggs/gram of feces was determined. For those animals with greater than a 75% reduction in eggs/gram of feces, the total worm passage was determined ante-mortem and the animals were necropsied (generally 14 days post treatment) and counts made of internal worms not passed.

Representative test results are shown in Tables 2–6 below.

TABLE 2

*Haemonchus contortus* worm eggs per gram of feces in sheep treated by a single intraruminal injection of 5 to 10 mg/kg bodyweight of [(4-trifluoromethoxyphenyl)sulfonyl][(trifluoromethyl)-sulfonyl]methane

| | Worm Eggs Per Gram of Feces (EPG) | | | | | | Percent |
|---|---|---|---|---|---|---|---|
| | | Days Following Treatment | | | | | |
| Dose | Pre* | 1 | 2 | 3 | 4 | 5–7* | EPG Reduction |
| 5 | 2233 | 2900 | 0 | 0 | 0 | 0 | 100 |
| 5 | 11367 | 4100 | 100 | 0 | 0 | 0 | 100 |
| 10 | 770 | 600 | 0 | 0 | 0 | 0 | 100 |
| 10 | 2667 | 2800 | 100 | 0 | 0 | 0 | 100 |

*Average of 3 days sampling

TABLE 3

*Haemonchus contortus* worm eggs per gram of feces in sheep treated by a single parenteral injection of 5 mg/kg bodyweight of [(3,4-dichlorophenyl)sulfonyl][trifluoromethylsulfonyl]methane

| | Worm Eggs Per Gram of Feces (EPG) | | | | | | Percent |
|---|---|---|---|---|---|---|---|
| | | Days Following Treatment | | | | | |
| | Pre* | 1 | 2 | 3 | 4 | 5–7* | EPG Reduction |
| IM | 2533 | 1000 | 600 | 300 | 100 | 550 | 78.3 |
| SC | 7167 | 3800 | 1700 | 1300 | 200 | 400 | 94.4 |

IM = intramuscular injection
SC = subcutaneous injection
*Average of 3 days sampling

TABLE 4

Helminthological data for sheep treated by a six-hour continuous intraruminal infusion of [(3,4-dichlorophenyl)sulfonyl][(trifluoromethyl)sulfonyl]methane

| | Worm Eggs Per Gram of Feces (EPG) | | | | | | Percent EPG Reduction | Total Worm Count[1] | Percent Worm Reduction |
|---|---|---|---|---|---|---|---|---|---|
| | | Days Following Treatment | | | | | | | |
| | Pre* | 1 | 2 | 3 | 4 | 5–7* | | | |
| | 1667 | 1100 | 1000 | 0 | 0 | 0 | 100 | 0 | 100 |
| Control | 533 | 900 | 800 | 900 | 900 | 900 | 0 | 188 | 0 |

Total Worm Counts for *Haemonchus contortus*
*Average of 3 days sampling
[1]At necropsy 7 days following treatment

TABLE 5

Helminthological data collected from calves treated by a single intraruminal or subcutaneous injection of a compound of the present invention

| Cmpd. | Dose | Worm Eggs Per Gram of Feces | | | | | | | | | % Worm Egg Reduction | Total Worm Counts[1] |
|---|---|---|---|---|---|---|---|---|---|---|---|---|
| | | Pre* | 1 | 2 | 3 | 4 | 5–7* | 9 | 11 | 14 | | |
| A | 10 SC | 600 | 100 | 0 | 100 | 100 | 150 | 200 | 200 | 200 | 66.7 | N/D |
| A | 10 SC | 433 | 100 | 100 | 200 | 200 | 150 | 100 | 100 | 100 | 76.9 | N/D |
| B | 10 IR | 400 | 500 | 800 | 400 | 300 | 233 | | | | 41.8 | 71 |
| B | 20 IR | 300 | 300 | 200 | 100 | 0 | 33 | | | | 89 | 152 |

Worm Egg Counts for *Ostertagia ostertagi*
Cmpd. A = [(4-trifluoromethoxyphenyl)sulfonyl][(trifluoromethyl)sulfonyl]methane
Cmpd. B = [(3,4-dichlorophenyl)sulfonyl][(trifluoromethyl)sulfonyl]methane
Single subcutaneous (SC) or intraruminal (IR) injection
[1] At necropsy 7 days following treatment
*Average of 3 days sampling

TABLE 6

Summary Table In vivo Test Results

| Compound | Host | Dose (mg/kg) | Route | EPG Reduction (%) | Percent Efficacy | | | | |
|---|---|---|---|---|---|---|---|---|---|
| | | | | | HC | Ost | Tricho | ASF | LBF |
| A | sheep | 15 | SQ | 100 | 100[a] | >95[a] | >95[a] | 90 (Day 13) | NA |
| A | sheep | 15 | IR | 100 | 100[a] | >95[a] | >95[a] | 90 (Day 11) | NA |

| Compound | Host | Dose (mg/kg) | Route | EPG Reduction (%) Day 7/Day 16[b] | Percent Efficacy | | | | |
|---|---|---|---|---|---|---|---|---|---|
| | | | | | HC | Ost | Tricho | ASF | LBF |
| B | sheep | 15 | SQ | 67/67 | 100 | 72 | 40 | 100 (Day 7) | NA |

| Compound | Host | Dose (mg/kg) | Route | EPG Reduction (%) Day 7/Day 13[b] | Percent Efficacy | | | | |
|---|---|---|---|---|---|---|---|---|---|
| | | | | | HC | Ost | Tricho | ASF | LBF |
| A | sheep | 5 | SQ | 100/96.7 | 98 | 0[c] | 99 | 75 (Day 4) | 0 |
| A | sheep | 5 | IR | 99.05/100 | 100 | 20[c] | 90 | 85 (Day 4) | 0 |
| A | sheep | 10 | SQ | 100/100 | 100 | 100 | 100 | 95 (Day 7) | 0 |
| A | sheep | 10 | IR | 100/100 | 100 | 0[c] | 100 | 80 (Day 7) | 0 |

| Compound | Host | Dose (mg/kg) | Route | EPG Reduction (%) Day 7/Day 13[b] | Percent Efficacy | | | | |
|---|---|---|---|---|---|---|---|---|---|
| | | | | | HC | Ost | Tricho | ASF | LBF |
| A | cattle | 2.5 | SQ | 95.3/96.3 | ND | ND | ND | NA | 0 |
| A | cattle | 5 | SQ | 100/99.1 | ND | ND | ND | 75 (Day 6) | 0 |
| A | cattle | 7.5 | SQ | 100/100 | ND | ND | ND | 65 (Day 7) | 0 |
| A | cattle | 10 | SQ | 92.7/100 | ND | ND | ND | 75 (Day 7) | 0 |
| A | cattle | 15 | SQ | 100/100 | ND | ND | ND | 85 (Day 10) 80 (Day 20) | 0 |
| Levamisole control | cattle | 2.6 | SQ | 100/100 | ND | ND | ND | 0 | 0 |

Cmpd. A [((4-trifluoromethoxy)phenyl)sulfonyl][(trifluoromethyl)sulfonyl]methane levamisole salt
Cmpd. B [((4-trifluoromethoxy)phenyl)sulfonyl][(trifluoromethyl)sulfonyl]methane tetramethylammonium salt
[a] Estimated efficacy
[b] Later fecal sample collected at necropsy
[c] Activity against *Ostertagia* difficult to interpret because of low numbers in the untreated control group.
ASF Adult stable fly
HC *Haemonchus contortus*
IR Intraruminal injection
LBF Larval blow fly
NA No activity
ND None detected
Ost *Ostertagia ostertagi*
SQ Subcutaneous injection
Tricho *Trichostrongylus sp.*

The test results indicate that compounds according to Formula I are effective against worms such as *Haemonchus contortus*. Compounds such as the following were found to be particularly effective in this regard:

[(4-chlorophenyl)sulfonyl][(trifluoromethyl)sulfonyl]methane;

[(4-trifluoromethoxyphenyl)sulfonyl][(trifluoromethyl)sulfonyl]methane;

[(3,4-dichlorophenyl)sulfonyl][(trifluoromethyl)sulfonyl]methane; and

[((4-trifluoromethyl)phenyl)sulfonyl][(trifluoromethyl)sulfonyl]methane.

[((4-trifluoromethoxy)phenyl)sulfonyl][(trifluoromethyl)-sulfonyl]methane levamisole salt.

[(3,4-dichlorophenyl)sulfonyl][(trifluoromethyl)sulfonyl]methane;

[((4-trifluoromethyl)phenyl)sulfonyl][(trifluoromethyl)-sulfonyl]meth ate;

[(2,4,5-trichlorophenyl)sulfonyl][(trifluoromethyl)sulfonyl]methane;

[(3-chloro-4-fluoro-phenyl)sulfonyl][(trifluoromethyl)-sulfonyl]methane;

[(4-chlorophenyl)sulfonyl][(trifluoromethyl)sulfonyl]methane; and

[((3-trifluoromethyl)phenyl)sulfonyl][(trifluoromethyl)-sulfonyl]methane.

Representative test results of in vivo applications are shown in Tables 7 and 8 below.

TABLE 7

Endectocide test in sheep
[(4-trifluoromethoxyphenyl)sulfonyl][(trifluoromethyl)sulfonyl]methane Percent insecticide activity following 48 hour in vitro exposure

| Dose | Day 0 | | 30 min. | | 5 hr. | | Day 1 | | Day 2 | | Day 3 | | Day 4 | | Day 5 | | Day 6 | | Day 7 | |
|---|---|---|---|---|---|---|---|---|---|---|---|---|---|---|---|---|---|---|---|---|
| | L | A | L | A | L | A | L | A | L | A | L | A | L | A | L | A | L | A | L | A |
| 10 | 0 | 0 | 0 | 80 | 0 | 100 | 0 | 100 | 0 | 90 | 0 | 100 | 0 | 90 | 0 | 100 | 0 | 90 | 0 | 100 |
| 10 | 0 | 13 | 0 | 20 | 0 | 100 | 0 | 100 | 0 | 100 | 0 | 100 | 0 | 90 | 0 | 100 | 0 | 70 | 0 | 100 |
| 5 | 0 | 0 | 0 | 0 | 0 | 0 | 0 | 60 | 0 | 30 | 0 | 20 | 0 | 10 | 0 | 10 | 0 | 10 | 0 | 0 |
| 5 | 0 | 0 | 0 | 0 | 0 | 50 | 0 | 80 | 0 | 90 | 0 | 30 | 0 | 10 | 0 | 20 | 0 | 0 | 0 | 20 |
| Control | 0 | 0 | 0 | 0 | 0 | 0 | 0 | 0 | 0 | 0 | 0 | 0 | 0 | 0 | 0 | 0 | 0 | 0 | 0 | 0 |

Single intraruminal (IR) injection of 5 or 10 mg/kg of body weight, in PEG 200.
L Larval blow fly
A Adult stable fly

EXAMPLES 25–35

Tests Against *Phormia regina* (blow fly) and *Stomoxys calcitrans* (stable fly) in Sheep and Cattle Various of the compounds to be employed in the present invention were evaluated for the control of the larval phase of the adult stage of *Stomoxys calcitrans* (stable fly), and for the control of the larval phase of *Phormia regina* (blow fly). The test procedures were as follows.

The respective compound was formulated, in many tests by simply dissolving it in polyethylene glycol 200 (PEG 200 Formulation), in other tests by dissolving it in polyethylene glycol 200 and ethanol. Each formulation was administered to the test animal as a single intraruminal or subcutaneous injection. Typically there were two animals in each treatment group and one-two animals in the vehicle control group.

Blood samples were taken from the animals after 30 minutes, five hours, one day, and daily thereafter post treatment. Serum samples were prepared and insecticidal activities were determined by exposure of the serum samples to larval and adult flies.

The results of in vivo blow fly and stable fly tests indicate that compounds according no Formula I are effective against blood sucking parasites such as insects. Among the compounds found to be therapeutically effective in this regard are:

[(phenyl)sulfonyl][(trifluoromethyl)sulfonyl]methane;

[(4-trifluoromethoxyphenyl)sulfonyl][(trifluoromethyl)-sulfonyl]methane;

TABLE 8

| | Endectocide test in calves | | | | | | | | | | |
|---|---|---|---|---|---|---|---|---|---|---|---|
| | Percent insecticide activity following 48 hour in vitro exposure | | | | | | | | | | |
| Agent[1] | Day 0 | 30 min. | 5 hr. | Day 1 | Day 2 | Day 3 | Day 4 | Day 5 | Day 6 | Day 7 | Day 14 |
| Cmpd A | 0 | 20 | 100 | 100 | 100 | 100 | 100 | 100 | 100 | 100 | ND |
| Cmpd A | 0 | 20 | 100 | 90 | 100 | 100 | 100 | 100 | 90 | 70 | ND |
| Cmpd B | 0 | 90 | 100 | 100 | 100 | 100 | 100 | 100 | 100 | ND | 90 |
| Cmpd B | 0 | 70 | 100 | 100 | 100 | 100 | 100 | 100 | 100 | ND | 100 |
| Control | 10 | 10 | 20 | 10 | 0 | 0 | 10 | 0 | 0 | 0 | 0 |

Single subcutaneous injection of 10 mg/kg bodyweight in PEG 200.
Cmpd. A = [(3,4-dichlorophenyl)sulfonyl][(trifluoromethyl)sulfonyl]methane
Cmpd. B = [(4-trifluoromethyoxyphenyl)sulfonyl][(trifluoromethyl)sulfonyl]methane
ND = not determined While the invention has been illustrated and described in detail in the foregoing description, the same is to be considered as illustrative and non restrictive in character, it being understood that only preferred embodiments have been shown and described and that all changes and modifications that come within the spirit of the invention are desired to be protected.

I claim:

1. A salt of a disulfonyl methane compound selected from the group consisting of

[phenylsulfonyl][(trifluoromethyl)sulfonyl]methane;

[(4-chlorophenyl)sulfonyl][(trifluoromethyl)sulfonyl]methane;

[(4-nitrophenyl)sulfonyl][(trifluoromethyl)sulfonyl]methane; and

[(3-nitro-4-chlorophenyl)sulfonyl][(trifluoromethyl)sulfonyl]methane with an anthelmintic compound selected from the group consisting of bephenium, diethylcarbamazine, levamisole, morantel, nicotine, piperazine, and pyrantel.

2. A salt of claim 1 wherein the disulfonyl methane compound is [(4-chlorophenyl)sulfonyl][(trifluoromethyl)sulfonyl]methane.

3. The salt of claim 2 with levamisole.

4. A salt of the disulfonyl methane compound [(3,4-dichlorophenyl) sulfonyl][(trifluoromethyl)sulfonyl]methane with an anthelmintic compound selected from the group consisting of:

bephenium, diethylcarbamazine, levamisole, morantel, nicotine, piperazine, and pyrantel.

* * * * *